(12) United States Patent
Sakazume et al.

(10) Patent No.: US 6,444,171 B1
(45) Date of Patent: Sep. 3, 2002

(54) SAMPLE PROCESSING SYSTEM (75) Inventors: Taku Sakazume, Hitachinaka; Hiroshi Mitsumaki, Mito, both of (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 09/364,061

(22) Filed: Jul. 30, 1999

(30) Foreign Application Priority Data

Jul. 31, 1998 (JP) .......................................... 10-217704

(51) Int. Cl.⁷ .............................................. G01N 35/02
(52) U.S. Cl. ............................. 422/65; 422/67; 436/47; 436/48
(58) Field of Search ............................. 422/67, 62, 65; 436/47, 48

(56) References Cited

U.S. PATENT DOCUMENTS

| | | | | |
|---|---|---|---|---|
| 5,350,564 A | * | 9/1994 | Mazza et al. | 422/63 |
| 5,902,549 A | * | 5/1999 | Mimura et al. | 422/65 |
| 5,972,295 A | * | 10/1999 | Hanawa et al. | 422/65 |
| 6,080,364 A | * | 6/2000 | Mimura et al. | 422/67 |
| 6,117,683 A | * | 9/2000 | Kodama et al. | 436/67 |

* cited by examiner

Primary Examiner—Nina Bhat
(74) Attorney, Agent, or Firm—Mattingly, Stanger & Malur, P.C.

(57) ABSTRACT

Waiting areas for allowing a plurality of sample racks to stop and wait are provided on by-pass line in each analysis unit. Sample racks introduced from ordinary sample inlet section or emergency sample inlet section, after waiting in the waiting area, are subjected to sample pipette operation by sample pipetting device. In the ordinary mode corresponding to ordinary sample processing, all of the stop positions of the waiting areas can be utilized, however, in the emergency mode corresponding to emergency sample processing, at least one or more of the stop positions of the waiting areas is prohibited to be used so as for the sample rack coming in to skip the stop position prohibited to be used.

10 Claims, 5 Drawing Sheets

SAMPLE PROCESSING SYSTEM

BACKGROUND OF THE INVENTION

The present invention relates to a sample processing system, and in particular, it relates to a sample processing system for physically or chemically processing biological samples such as blood and urine.

In a case where a plurality of samples comprising biological samples such as blood and urine are to be processed and analyzed, a many number of sample containers each containing a sample are held and carried in a holder which is called a sample rack for their processing. As a method for pipetting a sample from such a sample rack to an analysis unit provided with an analyzer function, the following two types are known.

One of them is a method as disclosed, for example, in JPA Laid-Open No. 3-285175, wherein a sample rack being conveyed from a sample rack supply unit to a sample rack collection unit is stopped on its way at an analysis unit for pipetting a sample from the sample rack on the transfer line to a reaction vessel in the analysis unit. The other one is a method as disclosed, for example, in JPA Laid-Open No. 9-281113, wherein a by-pass line is provided within each analysis unit which is arranged along the main conveyer line for allowing a sample rack being conveyed on the main conveyer line to be transferred to the by-pass line and for pipetting a sample with a pipetter from the sample rack on the by-pass line to a reaction vessel in the analysis unit.

In order for many numbers of samples to be efficiently processed by a plurality of sample processing units such as a centrifuge unit, a pipetter unit for pipetting child samples from a parent sample, analysis unit and the like, it is preferable to construct the system such that a sample rack carrying samples is supplied without intervals to a position where samples are to be processed thereby minimizing a sample waiting time for each sample processing unit. For this purpose, it is effective to provide for a method whereby a sample rack waiting area is provided for allowing a plurality of sample racks to wait in the vicinity of a sucking or sampling position of each analysis unit, then moves the next sample rack to the sampling position thereof immediately after pipetting from the preceding sample rack is completed.

However, in an arrangement of the system with provision of the waiting area, there arises a problem when an emergency sample which must be analyzed urgently is requested to be processed that the emergency sample will have to wait until a lot of ordinary samples waiting in queue on the waiting area are treated completely. Namely, in both cases of JPA Laid-Open No. 3-285175 where a lot of sample racks are already waiting on the conveyer line prior to starting the transfer of the emergency sample, and of JPA Laid-Open No. 9-281113 where a lot of ordinary sample racks are waiting on the by-pass line prior to starting of the transfer of the emergency sample, a result of processing of the emergency sample cannot be obtained in a short period of time.

SUMMARY OF THE INVENTION

An object of the invention is to provide a sample processing system which can process a lot of samples efficiently and continuously, and also can minimize a waiting time for an emergency sample that must be processed urgently.

A sample processing unit in a sample processing system according to the invention is provided with a sample aliquoter for pipetting a sample from the sample rack. A ordinary sample rack having ordinary samples which is introduced from a ordinary sample inlet portion or an emergency sample rack having emergency samples which is introduced from an emergency inlet portion is transferred to a sample processing unit by rack transfer means. A waiting area for allowing the sample rack prior to pipetting to wait is formed, for example, between the ordinary sample inlet portion and the sample processing unit, or on the by-pass line within the sample processing unit.

In a ordinary mode corresponding to the ordinary processing, the sample processing unit and/or the rack transfer means are controlled such that the number of sample racks that can be waited in the waiting area or items of their analysis becomes a predetermined number. In an emergency mode corresponding to an emergency processing, the sample processing unit and/or the rack transfer means are controlled such that the number of sample racks that can be waited in the waiting area or the number of items of analysis becomes smaller than the above-mentioned predetermined number.

Items to be monitored in the waiting area may include, in addition to the number of sample racks and the number of analysis items, a maximum number of pipetting scheduled or a maximum wait time until its pipetting. When an emergency sample processing is scheduled, the mode of operation is changed from the ordinary mode corresponding to the routine processing to the emergency mode corresponding to the emergency processing such that the number of waiting and/or waiting time in the emergency processing mode is minimized.

According to a preferred embodiment of the invention, there are provided a plurality of sample processing units and a designation device for giving a designation signal to each sample processing unit such that it can cope with the emergency processing mode. In the emergency processing mode, the number in waiting (numbers of sample racks, analysis items, maximum pipetting scheduled and so on) and waiting time according to a plurality of levels are changed, thereby allowing to select a preferred level or adjust thereto by the designation unit. Further, by dividing one day or its operation time into a plurality of time bands, it becomes possible appropriately to select or adjust a level of emergency processing mode according to each time band. Selection or adjustment of such levels is preferably done via a screen display included in the designation device.

BRIEF DESCRIPTION OF THE DRAWINGS

FIGS. 2 (A)–(D) show transfer conditions of a sample rack in the embodiment of FIG. 1;

DESCRIPTION OF THE PREFERRED EMBODIMENTS

With reference to FIGS. 1–4, a sample processing system according to a preferred embodiment of the invention will be described below.

Figure 1:
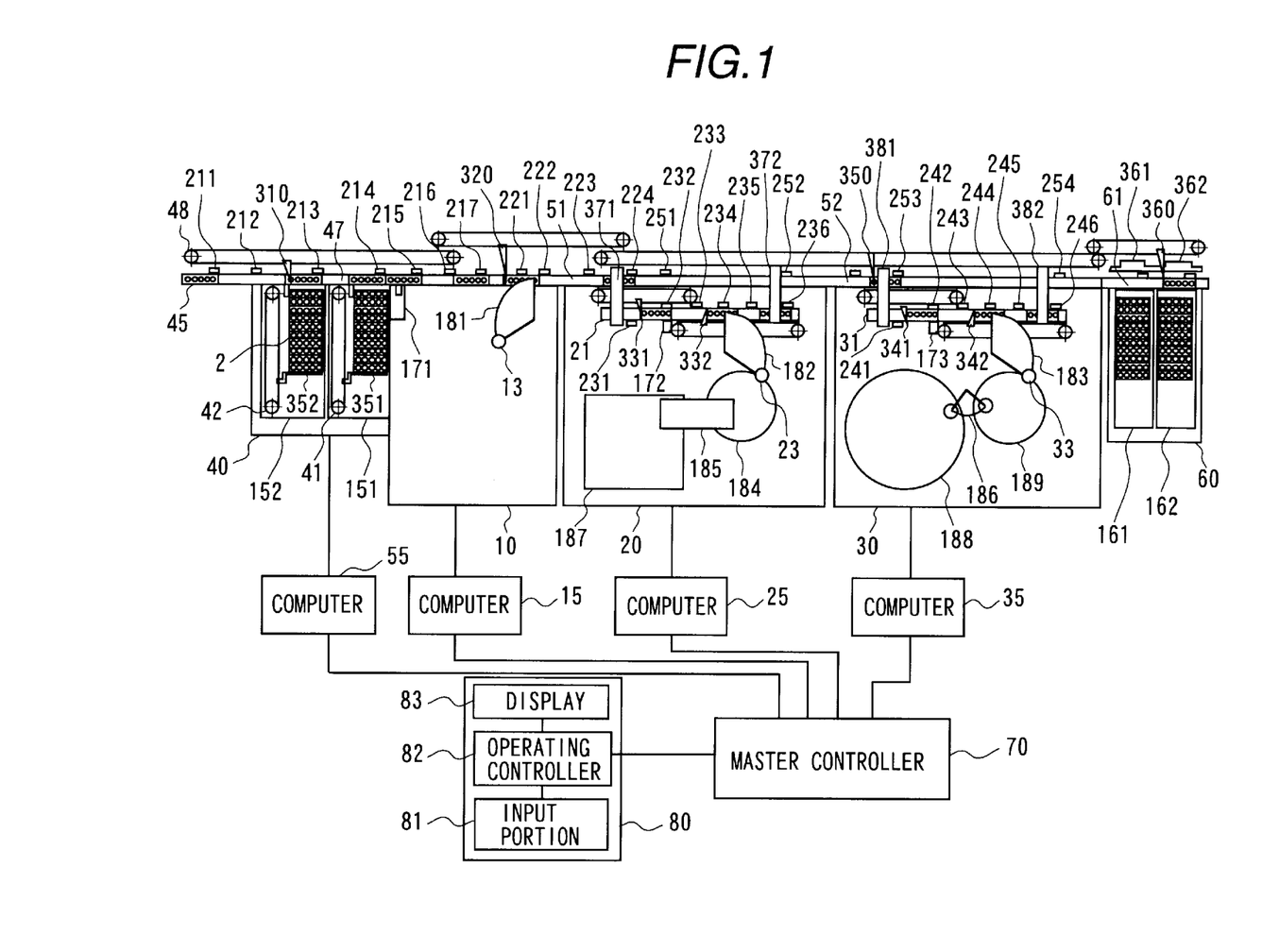
FIG. 1 is a plan view of a schematic arrangement of an embodiment according to the invention.

With reference to FIG. 1, two rack trays 151 and 152 are removably installed in a ordinary sample inlet unit 40. A many number of sample racks 2 which are arranged in order can be accommodated in each rack tray. A sample rack 2 on each rack tray can be pushed forward to a supply line 47 one by one by a lever 351 or 352 which is movable in horizontal directions actuated by a lever actuator 41 or 42. Sample rack 2 in an example of FIG. 1 is a box-type container holder that holds five test sample containers, however, the type of sample rack 2 and the number of test sample containers are not limited thereto, and many other types and modifications which can hold more than one sample containers and can be conveyed on a conveyer line can be contemplated within the scope of the invention.

A sample rack to be set in a ordinary sample inlet unit 40 is designed to hold sample containers which contain ordinary samples which can be processed routinely without need of emergency processing. An emergency sample inlet unit 45 is installed in the upper stream of the supply line 47 on which samples are conveyed. A sample rack which holds sample containers each containing an emergency sample which needs to have a result of its processing urgently is set in this emergency sample inlet unit 45. A sample rack which is set at a position 211 of an emergency sample reception of emergency sample inlet unit 45 is transferred to a position 217 for delivery to the conveyer line in precedence to a sample rack from the ordinary sample inlet unit 40.

In a system of FIG. 1, three different analysis units are arranged as sample processing units between the ordinary sample inlet unit 40 and a rack collection unit 60. Analysis unit 10 is a sample processing unit for analyzing and measuring electrolytic components by a measurement unit having an ionic selection electrode. A sample is pipetted from a sample rack on the conveyer line to a sample dilution container 13 provided within analysis unit 10 via a pipette nozzle of a sample pipetter 181, and then the sample, after being diluted in a dilution solution, is introduced to the measurement unit where respective ions of sodium, kalium, chlorine and the like are measured.

Analysis units 20 and 30 are sample processing units wherein a sample is mixed with a reagent to react therewith, and a colored solution resulting from the reaction is measured using an optical measurement apparatus such as absorption photometer.

Rack collection unit 60 accommodates in its rack tray 161 or 162 the sample rack 2 conveyed thereto having samples which were processed. The sample rack arriving at a collection line 61 of rack collection unit 60 is positioned at an entry to rack trays 161 or 162 by a rack transfer unit 360 which is actuated by a belt drive, then pushed into a corresponding rack tray by a rack pusher 361 or 362.

The rack conveyer line is comprised of supply line 47, a first conveyer line 51, a second conveyer line 52, and collection line 61. The first conveyer line 51 positions a first sample container on the sample rack delivered from the supply line 47 at a sample sucking or sampling position 221, moves the sample rack forward corresponding to each one of the sample containers with a progress of pipetting operation by sample pipetter 181, and then, after confirmation of completion of pipetting of the final sample container at sampling completion position 222, delivers the same via an intermediate position 223 to be positioned at a delivery position 224 through which to be delivered to a by-pass line 21 in analysis unit 20. Transfer of the sample rack on the first conveyer line 51 is accomplished by pushing forward the tail end of the sample rack thereon by a rack transfer unit 320 which is driven by the belt drive.

The second conveyer line 52 can convey the sample rack from a rack receiving position 251 at which sample rack 2 is received from the first conveyer line 51 to a next analysis unit via a rack receiving position 252 at which the sample is received from a by-pass line 21 of analysis unit 20, a rack delivery position 253 at which the sample is delivered to a by-pass line 31 of analysis unit 30, a rack receiving position 254 for receiving the sample rack from by-pass line of analysis unit 30 and the like. Transfer of the sample rack on the second conveyer line is accomplished by a rack transfer unit 350 which is driven by the belt drive and pushes forward the tail end of the sample rack.

Figures 2A, 2B:
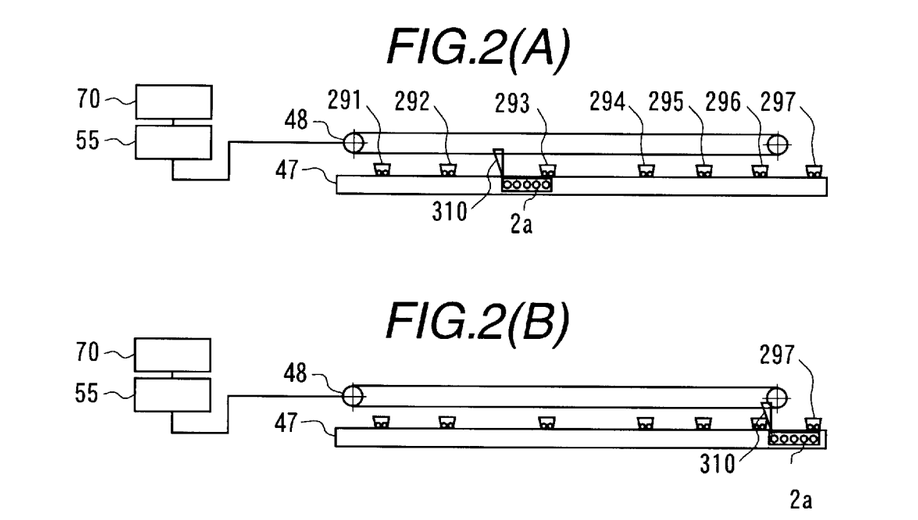
Figure 2C:
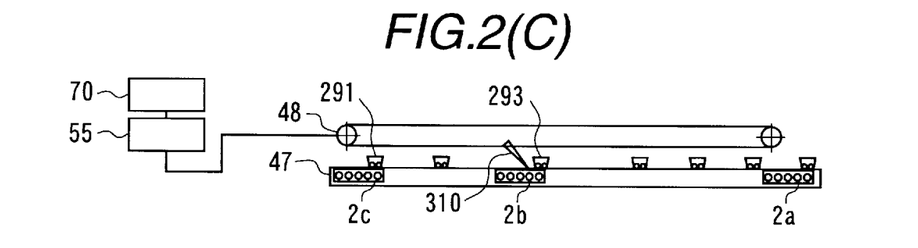
Figure 2D:
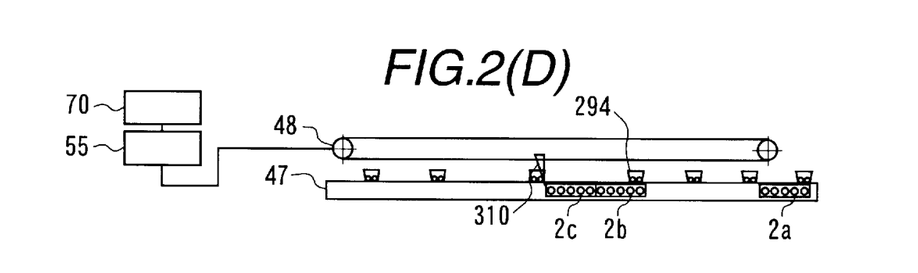

Now, a function of the rack transfer means will be described in reference to FIGS. 1 and 2. FIG. 2 illustrates a mode of transfer of a sample rack on supply line 47, however, it is not limited thereto, and this transfer mode is applicable basically to other transfer modes on other conveyer lines and by-pass lines likewise.

A plurality of rack detectors 291–297 are disposed along the supply line 47, and each of these rack detectors corresponds to each of positions 211–217 on the supply line 47. Namely, a sample rack at emergency sample receiving position 211 is detected by rack detector 291, a sample rack arriving at intermediate position 212 is detected by rack detector 292, a sample rack pushed forward from rack tray 152 to receiving position 213 is detected by rack detector 293, a sample rack pushed forward from rack tray 151 to receiving position 214 is detected by rack detector 294, a sample rack arriving at a read position 215 of ID information reader 171 is detected by rack detector 295, a sample rack positioned at intermediate position 216 is detected by rack detector 296, and a sample rack arriving at a delivery position 217 to the first conveyer line is detected by rack detector 297, respectively.

A belt drive unit 48 has an endless belt stretched between a drive pulley connected to a drive power source and another pulley. A rack transfer device 310 is fixed to this endless belt. An arm of the rack transfer device 310 can rotate a predetermined angle in a forward direction. In case of pushing the tail end of sample rack 2a as in FIG. 2(A), its rotation is prevented, however, in case where the rack transfer device 310 moves backward (return) relative to the sample rack which is advancing from rack detector 291 on the side of the emergency sample inlet unit to rack detector 297 at delivery position 217 to the first conveyor line 51 as indicated in FIG. 2(C), the arm thereof becomes rotatable thereby allowing the rack transfer device to return without affecting the motion of the sample rack. Other rack transfer devices in FIG. 1 have the same arrangement as described above.

As shown in FIG. 2(A), suppose that a ordinary sample rack 2a is pushed from rack tray 152 to receiving position 213, upon detection thereof by rack detector 293, rack transfer device 310 moves the ordinary sample rack 2a to the position of rack detector 297 by pushing forward the tail end of the sample rack 2a, as indicated in FIG. 2(B). Then, suppose that another ordinary sample rack 2b is pushed out from rack tray 152 onto supply line 47, and immediately after that, an emergency sample rack 2c is introduced into emergency sample inlet unit 45. In this case, the ordinary sample rack 2b is sensed by rack detector 293, and immediately after that, the emergency sample rack 2c is sensed by rack detector 291. Thereby, the rack transfer device 310 is caused to return from the state of FIG. 2(C) to a start end position of supply line 47 so as to move the emergency sample rack 2c by pushing the tail end thereof. Further, as indicated in FIG. 2(D), the rack transfer device 310 moves forward both the ordinary sample rack 2b and the emergency sample rack 2c, then stops its pushing operation in response to a signal that the ordinary sample rack 2b is sensed by rack detector 294.

The second analysis unit 20 is comprised of a sample pipetting device 182 having a pipette nozzle, a reaction disk 184 on which a many number of reaction containers are arranged, a reagent refrigerator 187 which accommodates a plurality of reagent bottles corresponding to a plurality of analysis items, and a dispenser type reagent supply device 185 for supplying a reagent to a reaction container 23 on the reaction disk 184. In each reaction container 23, a chemical reaction or immunity reaction between the sample and the reagent proceeds, and optical properties of its reaction solution are measured.

The third analysis unit 30, although differs from the second analysis unit in the method of supplying reagents, is the same in the method of measurement of reaction solutions. Its sample pipetting device 183 having a pipette nozzle aspirates a part of the sample into its pipette nozzle from the sample rack positioned at sample pipetting position 244 on by-pass line 31, and discharges the part of the sample in the pipette nozzle into one of the plurality of reaction containers 33 arranged on the reaction disk 189. A many number of reagent bottles are disposed on reagent turn table 188, and a preferred reagent is aspirated therefrom by reagent pipetting mechanism 186 having a reagent pipette nozzle to be discharged into reaction container 33. A reaction solution resulting from the reaction between the sample and the reagent in the reaction container is measured its optical properties by an optical photometer disposed along reaction disk 189, and concentrations of respective analysis items related to the sample are computed.

The second analysis unit 20 and the third analysis unit 30 are provided with built-in type by-pass lines 21, 31 of the same construction. Further, these analysis units 20, 30 have sample rack transfer devices 371, 372, 381, 382. A sample rack arriving at delivery positions 224, 253 to each analysis unit is moved over to rack reception positions 231, 241 on by-pass line 21, 31 by transfer devices 371, 381. Further, the sample rack after completing its pipetting processing is transferred from delivery positions 236, 246 on by-pass lines 21, 31 to rack reception positions 252, 254 on the second conveyer line 52 by transfer devices 372, 382.

By-pass lines 21, 31 are provided along the second conveyor line 52, and has a plurality of positions at which the sample rack can stop. By way of example of FIG. 1, the sample rack is allowed to stop at such positions as rack reception positions 231, 241, ID information read positions 232, 242, intermediate positions 233, 243, sample sucking or sampling positions 234, 244, sampling complete positions 235, 245, and delivery positions 236, 246. By provision of a plurality of intermediate positions 233, 243, not limiting to one, the number of sample racks that can be accommodated increases.

In order to transfer the sample rack on by-pass line 21, two rack transfer devices 331 and 332 which are driven by a belt drive respectively are provided. Further, in order to transfer the sample rack on by-pass line 31, two rack transfer devices 341 and 342 which are driven by a belt drive respectively are provided. Rack transfer devices 331, 341 take part in transferring the sample rack from the sample reception position to intermediate positions 233, 243 which are in the pre-stage of sample sucking or sampling positions 234, 244. On the other hand, rack transfer devices 332, 342 function to transfer the sample rack from the intermediate positions 233, 243 to delivery positions 236, 246.

The sample transfer or conveyor method for moving the sample rack on the conveyor line and/or the by-pass line in FIG. 1 is described by way of example of moving the sample rack by pushing forward the tail end thereof, however, it is not limited thereto, and a known method using a belt conveyor can be adopted to construct the transfer line itself. Further, in the example of FIG. 1, the first and the second main transfer lines are used, however, it is not limited thereto, and a single main line or a plurality of transfer line sections corresponding to respective analysis units can be used as well.

Three kinds of analysis units are used as sample processing units in the example of FIG. 1. However, other sample processing units can be included such as a centrifuge unit for separating components by a difference in specific gravity thereof, a cap opener unit for opening the cap of a sample container having a cap, and an aliquoter for pipetting a part of the sample from a parent sample container into a child sample container, they being disposed between the ordinary sample inlet unit 40 and the first analysis unit 10 in an arrangement of the invention for allowing the sample rack to be selectively transferred to each unit.

In FIG. 1, an analysis unit control section 15 is a computer which controls the operation of the first analysis unit 10 and executes arithmetic operation of measured data. An analysis unit control section 25 is a computer which controls the operation of the second analysis unit 20 and executes arithmetic operation of measured data. An analysis unit control section 35 is a computer which controls the operation of the third analysis unit 30 and executes arithmetic operation of measured data. Further, a conveyor line control section 55 is a computer which controls the transfer operation of each sample rack on the basis of judgment of a rack detection signal in the ordinary sample inlet section 40, emergency sample inlet section 45, supply line 47, first conveyor line 51, second conveyor line 52 and rack collection section 60, and by controlling respective operations of each rack transfer device, the movable lever, and the rack pushing device. Still further, master control section 70 is a computer which supervises three analysis control sections and the transfer line control section so as to ensure that the system operates smoothly.

A control panel section 80 connected to the master control section 70 is comprised of an input section 81, an operation control section 82 and a display section 83. The input section 81 includes a keyboard, a mouse serving as a pointing device relative to a display screen, and a touch panel. Display section 83 has a printing device in addition to a display device such as a CRT or liquid crystal.

A rack ID information indicative of its rack number and rack type is shown on a predetermined area of the sample rack serving as a container holder. Further, a sample ID information indicative of the number of a sample contained in a sample container, contents of its processing, analysis items and the like is shown as a mark such as a bar code on the outer wall of each sample container held on the sample rack 2. By way of example of FIG. 1, its rack ID information and sample ID information are shown in a bar code.

A bar code reader 171 which is an ID (identification) information reader disposed along the supply line 47 reads out a rack ID and/or sample ID of the sample rack which is positioned at read-out position 215, and transmits a result of its read-out operation to the transfer line controller (computer) 55. On the basis of this information transmitted, process contents for a corresponding sample rack are determined specifically, and particular analysis units to which the sample rack must be transferred and analysis items of each sample requiring specific pipetting are registered in a memory of the control section.

A bar code reader 172 which serves as an ID information reader and is disposed along by-pass line 21 of the second analysis unit 20 reads out a rack ID and/or sample ID of the sample rack received from the conveyor line and transmits the same to the analysis unit control section 25. A bar code reader 173 which is disposed along the by-pass line 31 of the third analysis unit 30 reads out ID information of the sample rack and transmits its result to the analysis unit control section 35. By the way, all of the master control section 70, conveyor line control section 55, analysis unit control sections 15, 25, 35 inclusive may be referred to as the control means or control section.

Figure 3:
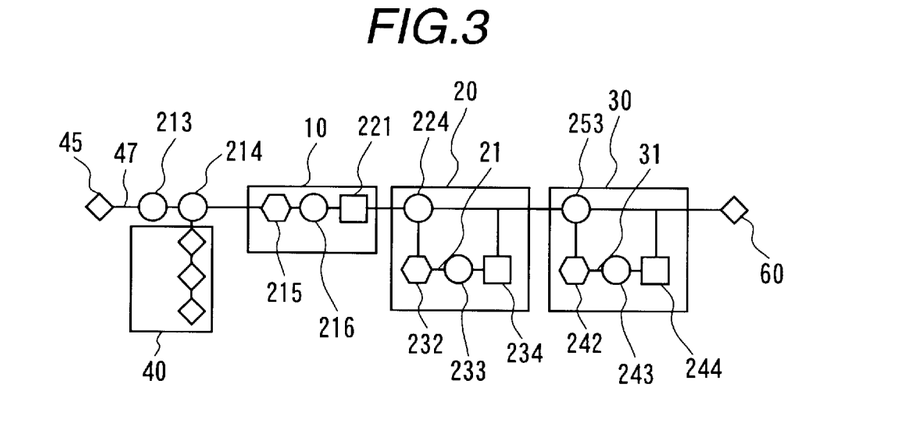
FIG. 3 shows stop positions of the sample rack in the ordinary processing mode.
Figure 4:
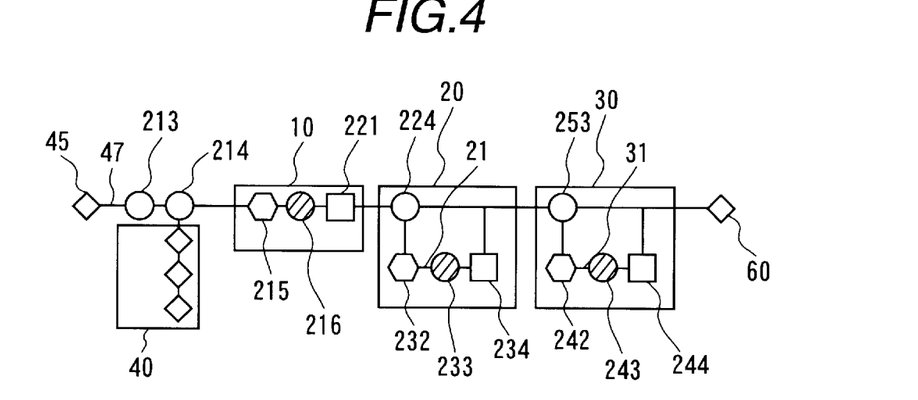
FIG. 4 shows waiting positions of the sample rack in emergency processing mode.

Now, in reference to FIGS. 3 and 4, stop positions of the sample rack waiting for pipetting operation and the number of such sample racks waiting for pipetting operation will be described by way of example of FIG. 1.

Sample rack 2 entered either from ordinary sample inlet section 40 or emergency sample inlet section 45 can stop over at every ones of or any ones selected of the first, the second and the third analysis units 10, 20, 30 before the same arrives at the rack collection section 60. In the first analysis unit 10, the sample rack 2 can stop at ID information read-out position 215, intermediate position 216, and sample sucking or sampling position 221. In the second analysis unit 20, the sample rack 2 can stop at delivery position 224, reception position 231, ID information read-out position 232, intermediate position 233, sample sucking or sampling position 234 and the like. Further, in the third analysis unit 30, the sample rack can stop at delivery position 253, reception position 241, ID information read-out position 242, intermediate position 243, sample sucking or sampling position 244 and the like.

Each intermediate position 216, 233 or 243 in each analysis unit is not limited to one, and a plurality of such positions can be provided. A waiting area for allowing the sample rack prior to each pipetting to wait therein includes ID information read-out position 215 and intermediate position 216 in the case of the first analysis unit 10, ID information read-out position 232 and intermediate position 233 on by-pass line 21 in the case of the second analysis unit, and ID information read-out position 242 and intermediate position 243 on by-pass line 31 in the case of the third analysis unit.

In the mode corresponding to the ordinary processing, a sample rack can be pushed out from the ordinary sample inlet section 40 onto reception position 213 and 214 on supply line 47, and supply line 47 can accept a sample rack from emergency sample inlet section 45.

In the mode corresponding to the ordinary processing, all positions corresponding to the waiting area of the sample rack prior to pipetting in each analysis unit where the sample rack can stop are monitored by each rack detector corresponding thereto, and thereby rack transfer devices 320, 331, 341 can position the sample rack at any of these all positions. In an example of the schematic diagram of FIG. 3, the number of sample racks that can be waited in each waiting area in each analysis unit is two in the case of the first analysis unit 10, two in the case of the second analysis unit 20, and two in the case of the third analysis unit. However, a predetermined number of sample racks that can be accommodated in each waiting area can be set at a greater number by increasing the number of respective intermediate positions, and respective predetermined numbers of sample racks that can be waited in respective waiting areas can be set at different values from each other.

In the mode corresponding to emergency processing, the number of sample racks allowed to wait in the waiting area in each of analysis units 10, 20, 30 is restricted to a number which is smaller than the predetermined maximum number of sample racks allowed to be accommodated in the waiting area in each analysis unit in the mode corresponding to the ordinary processing. That is, operation of rack transfer means such as rack transfer device 320 is controlled by controller (computer) 70 such that no sample rack is at stoppage at intermediate position 216 in the first analysis unit 10 as indicated by a shadowed 216 in FIG. 4. More specifically, the operation of rack transfer device 320 is controlled such that a sample rack 2 the rack ID and sample ID of which are read out at ID information read-out position 215 is caused to skip over intermediate position 216 to be stopped at sample pipetting position 221.

Further, operations of rack transfer devices 331, 341 in the second and the third analysis units are controlled by controllers (computers) 25, 35 such that no sample rack is at stoppage at intermediate positions 233, 243 in the second and the third analysis units. More specifically, the sample racks at stoppage at ID information read-out position 232, 242 are moved skipping over intermediate positions 233, 243 to be positioned at sample sucking or sampling positions 234, 244.

In the mode corresponding to the emergency processing, with respect to the restriction conditions on the numbers of sample racks allowed to wait in the waiting area in each analysis unit and/or analysis items, a plurality of levels (stages) can be pre-stored in the controllers (70, 25, 35) from which to select an appropriate level according to necessity. For example, in a relatively lower level in the emergency processing mode, the number of waiting positions in each analysis unit is decremented by one from the number thereof preset in the mode corresponding to the ordinary processing as described above. In an intermediate level, the number of waiting positions is decremented by two from the number thereof preset in the ordinary processing mode. In a most stringent level, it is controlled such that no sample rack at all is allowed to wait in the waiting area in each analysis unit, and feeding operation of any ordinary sample from the ordinary sample inlet section 40 to the supply line 47 is interrupted, and that an emergency sample rack from the emergency sample inlet section 45 is ensured to be transported to its sample pipetting position without interference by any ordinary sample rack present in its way.

For example, suppose that in the waiting area on by-pass line 21 in the second analysis unit 20, there exist two intermediate positions and one ID information read-out position in the ordinary processing mode, a predetermined number of sample racks allowed to wait in the ordinary processing mode is three. In contrast, in the emergency processing mode, and in particular, in the lower level thereof, the number of sample racks allowable to wait becomes two wherein one intermediate position can be skipped. In the intermediate level thereof, the number of sample racks allowable to wait becomes one wherein two intermediate positions can be skipped. In the most stringent level thereof, the number of sample racks allowable to wait becomes zero because even the ID information read-out position is skipped.

When it becomes necessary to change the operation mode of the sample processing system of the invention while the same is operating in the ordinary processing mode such as to operate in the emergency processing mode and vice versa, this change can be instructed through operation section 80 in FIG. 1. In this case, operation section 80 functions as a designation device for designating application of respective modes of operation.

Figure 5:
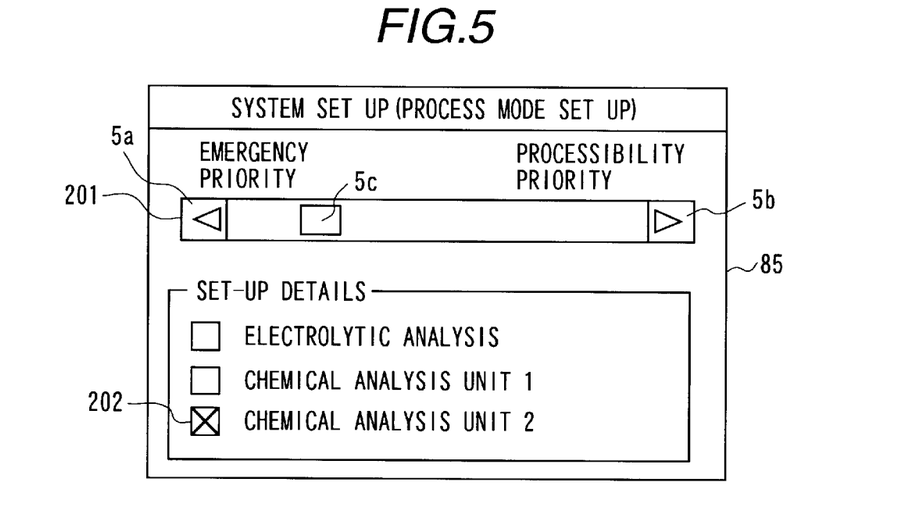
FIG. 5 shows an example of process mode set-up display screens on the designation display device.

FIG. 5 is a diagram indicative of a designation aspect of the invention for selectively designating a process mode for each analysis unit, in which one of the process mode setting screens is displayed on the display unit of display section 83. On a mode set-up screen 85, there are displayed a level display row 201 and a detail set-up row for selecting analysis units. In an example of FIG. 5, a unit designation mark is not indicated in the check boxes of an electrolytic analysis unit and a chemical analysis unit 1, however, a unit designation mark 202 is indicated in the check box of a second chemical analysis unit 2. This is a result of designation that the emergency mode corresponding to emergency processing is applied exclusively to chemical analysis unit 2 (which corresponds to the third analysis unit 30 in FIG. 1), and that the ordinary mode corresponding to ordinary processing mode is applied to other analysis units. As described above, each chemical analysis unit can select any mode individually.

In FIG. 5, level display row 201 has level designation buttons 5a and 5b. In each analysis unit, when no designation by unit designation mark 202 is given, a mover 5c is positioned closest to the level designation button 5b. That is, it indicates that all of the analysis units are to operate in the ordinary mode corresponding to the ordinary processing. The position of the mover box 5c can be changed to plural steps by operation of level designation buttons 5a and 5b. When designation button 5a is clicked, the box 5c moves to the left and when designation button 5b is clicked, the mover 5c moves to the right. Except when the mover 5c is positioned closest to the designation button 5b, an emergency mode corresponding to the emergency processing is applied, then as the position of the mover 5c approaches toward the level designation button 5a, it indicates that a severe level is applied wherein the number of sample racks that can be waited in the waiting area in each analysis unit, or the number of analysis items, is limited severely.

Position information of mover 5c is identified by the control section, then the restriction conditions regarding the number of sample racks that can wait in the waiting area in an analysis unit which corresponds to the designation, or the number of analysis items that can be analyzed, are in an appropriate level in response to the position of the mover 5c. In the example depicted in FIG. 5, an emergency processing mode is applied only to one of the analysis units, however, it is not limited thereto, and its emergency processing mode can be applied to more than two analysis units or to all of the analysis units as well. Still further, by partially modifying the mode set-up screen 85 it can be arranged such that a level display row is provided corresponding to each analysis unit so as to enable to construct respective analysis units to operate in respective emergency processing modes which differ in levels from each other. As described above, the level display row 201 in FIG. 5 functions as means for adjusting or selecting an available waiting level in the emergency mode corresponding to emergency processing requirement.

Figure 6:
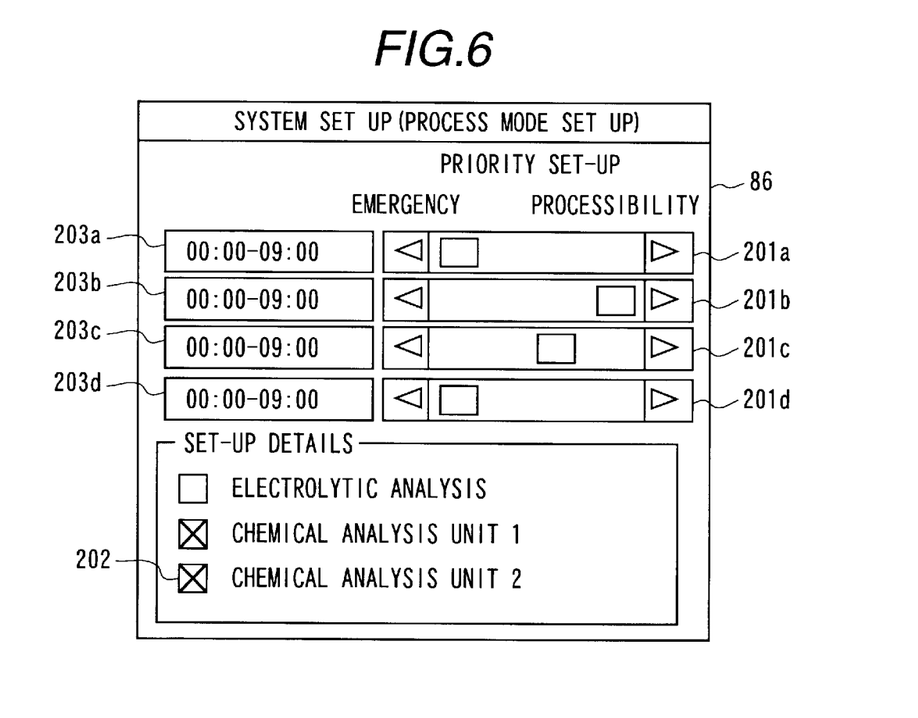
FIG. 6 shows another example of process mode set-up display screens on the designation display device.

FIG. 6 is a diagram indicative of another example of the processing mode set-up screens in the processing mode designation device of the invention. A mode set-up screen 86 displays: a plurality of time band display rows 203a, 203b, 203c, 203d for displaying a plurality of time bands; a plurality of level display rows 201a, 201b, 201c, 201d provided corresponding to each time band; and a detail set-up table where respective analysis units disposed in the sample processing unit of the invention and having respective waiting areas for allowing to wait sample racks prior to pipetting to wait are shown. Each level display row has a level designation button and a movable box, and has the same function of level adjustment or selection as in the case of FIG. 5. A designation method for designating to apply an emergency processing mode or a ordinary processing mode to the analysis unit is done in the same manner as in the case of FIG. 5.

In the example of FIG. 6, one day is divided into four time bands, and an appropriate level is adjusted or selected corresponding to the number of sample racks that can wait in the waiting area of each analysis unit or the number of allowable analysis items according to each time band selected. In FIG. 6, it is arranged such that a processing mode can be selected according to its time band and a level can be selected in the emergency processing mode, however, it is not limited thereto, and also it can be arranged such that a week is divided into week days, and a level adjustment can be executed according to each week day. In FIG. 6, a time band from 09:00 to 12:00 is operated in the ordinary processing mode to facilitate processing of a great number of samples resulting from many visiting patients to the hospital. A time band from 12:00 to 16:00 is operated in a slow-moving level with a small skip number in the emergency processing mode because it is necessary to test many number of samples coming from hospitalized patients. Time bands from 16:00 to 00:00 and from 00:00 to 09:00 are operated in a most severe level in the emergency corresponding process mode for processing samples mainly from emergency patients.

Figure 7:
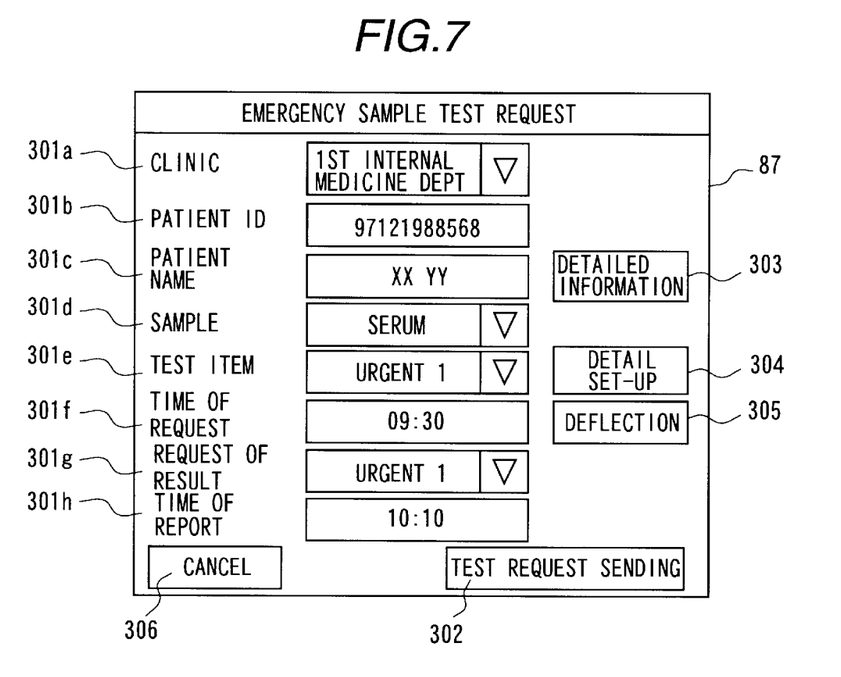
FIG. 7 shows an example of displays of a request for processing emergency samples entered via an operation device at a sample test requester.

Instead of designation of a processing mode by the operator through the operation section 80 in FIG. 1, it is also possible to execute mode switching automatically. In this case, the sample processing system of the invention is connected to a host computer in the hospital allowing communication therebetween, and an operation unit disposed in a clinic or the like which requests sample testing is connected to the host computer. FIG. 7 shows an example of screens for requesting emergency sample testing in advance entered from the operation unit at the clinic.

Input screen 87 in FIG. 7 includes an input row 301a indicating a sample test requesting section, an input row 301b indicating patient's ID, an input row 301c indicating patient's name, an input row 301d indicating a sample type (material), an input row 301e indicating a request item, a request time input row 301f, a result request input row 301g, an input row 301h indicating a desired report time scheduled, and the like. The input screen 87 also includes a test request transmission button 302, process mode detail set-up related buttons 303 and 304, a change button 305 for changing test conditions, and a cancel button 306. After inputting necessary items into respective input rows, when inspection request send button 302 is operated, an advance notice of request for processing emergency samples is sent to the master control section. In response to this advance notice of request, the control section changes the process mode of each analysis unit from the ordinary processing mode to the emergency processing mode in preparation of entry of a sample rack having emergency samples.

Next, with reference to FIGS. 8 and 9, another embodiment of the invention will be described in the following. Of a plurality of analysis units in FIG. 8, a first analysis unit 100a is provided for analyzing and measuring electrolytic components in the sample, and a second and a third analysis units 100b and 100c are provided for analyzing chemical items. Parts attached with the same symbols as in the embodiment of FIG. 1 have the same functions thereof. Different features of the embodiment of FIG. 8 different from those of the first embodiment of FIG. 1 reside in that both the second and the third analysis units are not provided with a by-pass line, and that a re-inspection buffer section 90 and a return line 95 are provided.

Each analysis unit has a waiting area for waiting a sample rack prior to pipetting on main conveyor line 57 and for allowing sample dispenser units 181, 182, 183 to dispense a part of samples from the sample rack positioned at sample pipetting position 221a, 221b, 221c on the main conveyor line 57 to their measurement sections. The sample rack after completion of its pipetting process is stored tentatively in re-inspection buffer section 90 until its measurement data are obtained. When no problem is found in the result of its measurement, the sample rack is moved to rack collection section 60. However, when abnormality is likely to exist in the result of measurements, the sample rack is delivered to return line 95 via rack sorting mechanism 92. The sample rack returned to the supply line 47 conveyed by the return line 95 is conveyed by the main conveyor line 57 to a desired analysis unit where to be subjected to a pipette processing once again.

Figure 9:
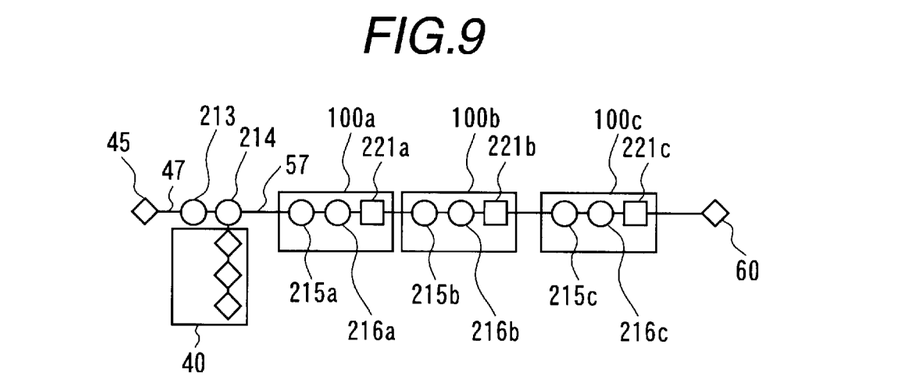
FIG. 9 shows sample rack stop positions of each analysis unit in the embodiment of FIG. 8.

As indicated in FIG. 9, each analysis unit has ID information read position 215a, 215b, 215c and intermediate position 216a, 216b, 216c in a pre-stage of sample dispensing position 221a, 221b, 221c, all of which forms each waiting area for allowing the sample rack before pipetting to wait. Also in this embodiment of the invention, in the processing mode corresponding to ordinary processing, all of the rack stop positions within each waiting area serves and functions as a predetermined number of waiting positions. However, in the emergency corresponding process mode, a part or all of these stop positions are excluded from the waiting positions, and the sample rack is moved skipping over these excluded positions in the same way as described in the embodiment of FIG. 1.

Figure 8:
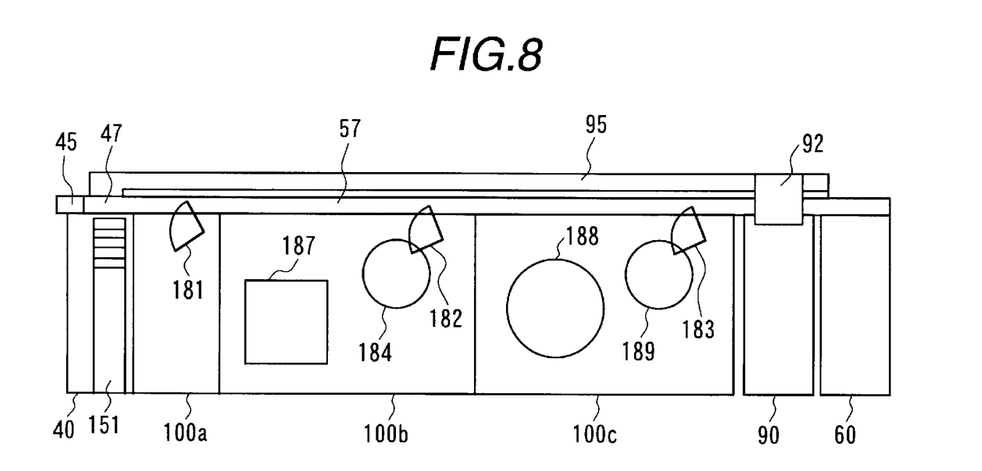
FIG. 8 is a plan view of an arrangement of another embodiment according to the invention.

Objects to be monitored by the controller regarding samples waiting in the waiting area in each analysis unit are not limited to the number of sample racks and/or the number of analysis items as described with respect to the embodiments of FIGS. 1 and 8. The objects of monitoring for restricting and determining a degree of sample racks that can wait in each waiting area may be a maximum number of pipetting scheduled until the last sample in the waiting area, or a longest waiting time until pipetting of the last sample in the waiting area. In any case, in the emergency corresponding process mode, an allowable value for the maximum frequency until its scheduled pipetting or the maximum waiting time until its pipetting is set by the control section to be smaller than the value in the ordinary process corresponding mode to ensure such that a time for an emergency sample newly introduced until it is processed for pipetting can be reduced substantially compared with the case of the ordinary processing mode.

According to the invention, a great number of samples can be processed continuously and efficiently in the ordinary mode of operation corresponding to ordinary sample processing, and a process waiting time for emergency samples which need urgent processing can be minimized by switching to the emergency process corresponding mode of the invention.

What is claimed is:

1. A sample processing system comprising: a sample processing unit including a sample pipetting device and a waiting area allowing a sample rack prior to pipetting operation to wait therein; an ordinary sample inlet section in which a sample rack holding ordinary samples is set; an emergency sample inlet section in which a sample rack holding emergency samples is set; and a sample rack transporter transporting the sample rack from said ordinary sample inlet section or said emergency sample inlet section to said sample processing unit, further comprising a controller instructing said sample processing unit to selectively switch between an ordinary mode corresponding to ordinary sample processing and an emergency mode corresponding to emergency mode processing, said sample processing unit being controlled on the basis of an instruction of said controller such that the number of sample racks allowed to wait in said waiting area or the number of analysis items becomes a predetermined value in said ordinary mode and such that the number of sample racks allowed to wait in said waiting area or the number of analysis items becomes smaller than said predetermined value in said emergency mode.

2. A sample processing system according to claim 1, further comprising: a plurality of said analysis units to which the sample rack is transported by said rack transporter; and a designation device designating to which of said plurality of said analysis units said emergency mode corresponding to emergency sample processing is to be applied.

3. A sample processing system according to claim 2, wherein said designation device comprises adjuster adjusting a level associated with the number of sample racks allowed to wait in the waiting area or the number of analysis items in the emergency mode corresponding to emergency sample processing.

4. A sample processing system according to claim 2, wherein said designation device comprises adjuster for adjusting a level associated with the number of sample racks allowed to wait in the waiting area or the number of analysis items for each one of a plurality of time bands.

5. A sample processing unit according to claim 3 wherein said designation device has a screen display displaying said level.

6. A sample processing unit according to claim 2, wherein said designation device comprises changing said ordinary mode corresponding to ordinary sample processing to said emergency mode corresponding to emergency sample processing on the basis of an emergency sample test request sent in advance from a sample test requester to said controller.

7. A sample processing unit according to claim 1, wherein said waiting area has a position to read out ID information attached on a sample container or the sample rack.

8. A sample processing unit according to claim 1, wherein said sample analysis unit is an analysis unit allowing a sample pipetted from the sample rack to react with a reagent and measure its result.

9. A sample processing unit comprising: a sample processing unit including a sample pipetting device and a waiting area for allowing a sample rack prior to pipetting operation to wait therein; a ordinary sample inlet section in which a sample rack holding samples is set; an emergency sample inlet section in which a sample rack holding emergency samples is set; and a sample rack transporter transporting the sample rack from said ordinary sample inlet section and/or said emergency sample inlet section to said sample processing unit, further comprising a controller controlling said sample processing unit such that a maximum scheduled frequency of pipetting operation for sample racks allowed to wait in said waiting area, or a longest waiting time in said waiting area until pipetting operation becomes a preset value in the ordinary mode corresponding to ordinary sample processing and such that said maximum scheduled frequency of pipetting operation for sample racks allowed to wait in said waiting area, or said longest waiting time in said waiting area until pipette operation becomes smaller than said preset value in the emergency mode corresponding to emergency sample processing, said sample processing unit selectively operating in said ordinary mode corresponding to ordinary sample processing or in said emergency mode corresponding to emergency sample processing.

10. A sample processing system comprising: a sample processing unit having a sample pipetting device; a ordinary sample inlet section in which a sample rack holding ordinary samples is set; and emergency sample inlet section in which a sample rack holding emergency samples is set; a sample rack transporter transporting the sample rack from said ordinary sample inlet section and/or said emergency sample inlet section to said sample processing unit, further comprising a waiting area waiting a sample rack prior to pipetting operation between said ordinary sample inlet section and said sample processing unit, and a controller instructing said sample processing unit to selectively switch between an ordinary mode corresponding to ordinary sample processing and an emergency mode corresponding to emergency sample processing, said rack transporter being controlled on the basis of an instruction of said controller such that the number of sample racks allowed to wait in said waiting area or the number of analysis items becomes a present value in the ordinary mode corresponding to ordinary sample processing and such that the number of sample racks allowed to wait in said waiting are or the number of analysis items becomes smaller than the preset value in the emergency mode corresponding to emergency sample processing.

* * * * *